United States Patent
Garzon et al.

(10) Patent No.: US 9,568,441 B2
(45) Date of Patent: Feb. 14, 2017

(54) GANTRY SYSTEM FOR CT IMAGING SYSTEM AND METHODS OF ASSEMBLING SAME

(71) Applicant: MORPHO DETECTION, LLC, Newark, CA (US)

(72) Inventors: Pedro Andres Garzon, Santa Clara, CA (US); Steven Leslie Hills, San Jose, CA (US); Anthony James Murch, Hayward, CA (US)

(73) Assignee: MORPHO DETECTION, LLC, Newark, CA (US)

( * ) Notice: Subject to any disclaimer, the term of this patent is extended or adjusted under 35 U.S.C. 154(b) by 217 days.

(21) Appl. No.: 14/607,967

(22) Filed: Jan. 28, 2015

(65) Prior Publication Data

US 2016/0219685 A1 Jul. 28, 2016

(51) Int. Cl.
G01N 23/00 (2006.01)
G01N 23/04 (2006.01)
A61B 6/03 (2006.01)

(52) U.S. Cl.
CPC ............. G01N 23/046 (2013.01); A61B 6/035 (2013.01); G01N 2223/308 (2013.01); G01N 2223/419 (2013.01)

(58) Field of Classification Search
None
See application file for complete search history.

(56) References Cited

U.S. PATENT DOCUMENTS

| | | | | | |
|---|---|---|---|---|---|
| 4,232,226 | A | * | 11/1980 | Huettner | A61B 6/02 378/147 |
| 4,232,914 | A | * | 11/1980 | Bowen, III | F16C 19/386 384/567 |
| 5,473,657 | A | * | 12/1995 | McKenna | A61B 6/035 378/15 |
| 5,784,428 | A | * | 7/1998 | Schmidt | A61B 6/56 378/15 |
| 7,010,081 | B2 | * | 3/2006 | Brunnett | A61B 6/035 378/15 |
| 8,796,893 | B2 | * | 8/2014 | Muth | A61B 6/035 310/156.01 |
| 2004/0062343 | A1 | * | 4/2004 | Brunnett | A61B 6/035 378/15 |
| 2010/0254640 | A1 | * | 10/2010 | Muth | A61B 6/035 384/107 |
| 2012/0148013 | A1 | * | 6/2012 | Zhang | A61B 6/03 378/4 |
| 2013/0148783 | A1 | * | 6/2013 | Ikawa | G01N 23/04 378/62 |
| 2014/0119515 | A1 | * | 5/2014 | McKenna | H05G 1/02 378/197 |

* cited by examiner

*Primary Examiner* — Andrew Smyth
(74) *Attorney, Agent, or Firm* — Armstrong Teasdale LLP

(57) ABSTRACT

A gantry system for use with a computed tomography imaging system is provided. The gantry system includes a frame, a support rail coupled to the frame, and a plurality of rollers. The frame defines an annular opening, and is configured to rotate about a rotational axis to collect imaging data from an object positioned within the opening. The support rail includes a canted sidewall having a radial inner surface and a radial outer surface. The plurality of rollers rotatably supports the support rail to enable rotation of the frame about the rotational axis. The plurality of rollers includes a first roller that engages the radial outer surface of the sidewall and a second roller that engages the radial inner surface of the sidewall.

20 Claims, 8 Drawing Sheets

GANTRY SYSTEM FOR CT IMAGING SYSTEM AND METHODS OF ASSEMBLING SAME

BACKGROUND

The embodiments described herein relate generally to computed tomography (CT) imaging systems, and more particularly, to rotating gantry systems for use in CT imaging systems.

Some CT imaging systems include a gantry having an x-ray source and one or more x-ray detectors. The gantry has an opening defined therein, and rotates about a central rotational axis to capture imaging data on an object positioned within the gantry opening using the x-ray source and x-ray detectors. The gantry is typically mounted to the CT imaging system by a bearing system that enables the gantry to rotate.

The gantry is often rotated at significant speeds to facilitate the collection of accurate imaging data during a helical scan of an object. As a result, at least some known CT imaging systems utilize costly and complex bearing systems to enable gantry rotation. For example, some known CT imaging systems utilize slew- or roller-type bearing assemblies having numerous rolling elements disposed between two bearing rings. Such bearing assemblies often utilize a large number of rolling elements to enable high-speed rotation of gantry. Additionally, the components of such bearing assemblies are often of significant size and, consequently, of significant cost. For example, bearing rings used in some gantry bearing assemblies have a diameter in excess of three feet. As a result, repairing and replacing components on gantry bearing assemblies often requires significant time and cost.

Additionally, gantry bearing assemblies utilized in CT imaging systems often include custom-made components that are designed for a particular CT imaging system (e.g., CT imaging systems manufactured by a specific CT imaging system manufacturer). Such custom components are often not easily replaced or interchangeable with other, more-readily available and less costly components, and thus further contribute to the cost and time associated with maintaining gantry systems in CT imaging systems.

BRIEF SUMMARY

In one aspect, a gantry system for use with a computed tomography imaging system is provided. The gantry system includes a frame, a support rail coupled to the frame, and a plurality of rollers. The frame defines an annular opening, and is configured to rotate about a rotational axis to collect imaging data from an object positioned within the opening. The support rail includes a canted sidewall having a radial inner surface and a radial outer surface. The plurality of rollers rotatably supports the support rail to enable rotation of the frame about the rotational axis. The plurality of rollers includes a first roller that engages the radial outer surface of the sidewall and a second roller that engages the radial inner surface of the sidewall.

In another aspect, a computed tomography (CT) imaging system is provided. The CT imaging system includes a base, a plurality of rollers coupled to the base, and a gantry assembly rotatably coupled to the base by the plurality of rollers. The plurality of rollers includes a first roller and a second roller. The gantry assembly includes a frame, a radiation source coupled to the frame, at least one detector coupled to the frame, and a support rail coupled to the frame. The support rail includes a canted sidewall having a radial inner surface and a radial outer surface. The first roller engages the radial outer surface and the second roller engages the radial inner surface.

In yet another aspect, a method of assembling a gantry system is provided. The gantry system includes a base and a plurality of rollers coupled to the base. The plurality of rollers includes a first roller and a second roller. The method includes providing a gantry assembly including a frame, a radiation source coupled to the frame, at least one detector coupled to the frame, and a support rail coupled to the frame, the support rail including a canted sidewall having a radial inner surface and a radial outer surface. The method further includes coupling the gantry assembly to the base such that the gantry assembly is rotatable about a rotational axis relative to the base. Coupling the gantry assembly to the base includes positioning the first roller into engagement with the radial outer surface of the sidewall and positioning the second roller into engagement with the radial inner surface of the sidewall.

DETAILED DESCRIPTION

Figure 1:
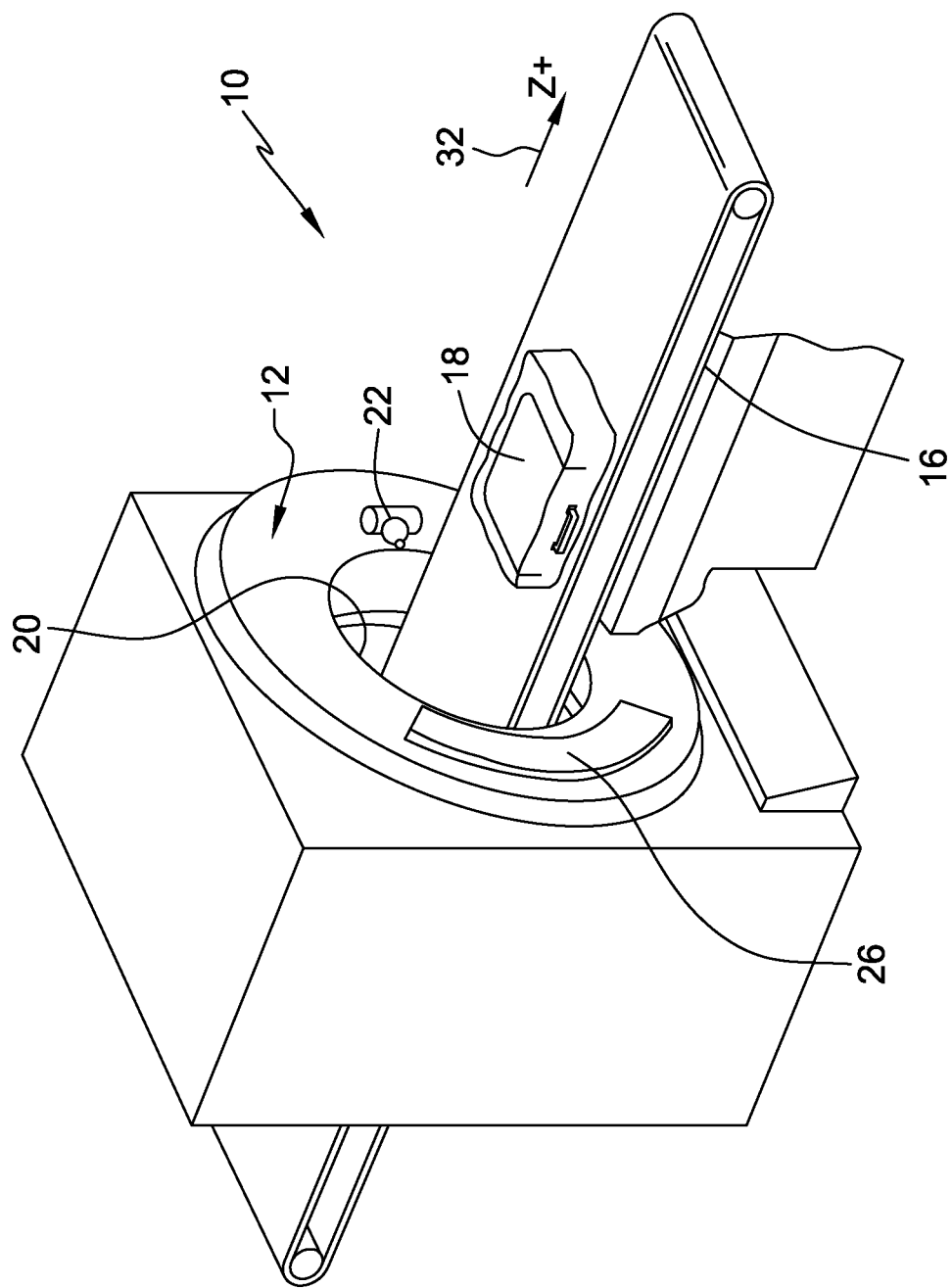
FIG. 1 is a perspective view of an exemplary CT imaging system.
Figure 2:
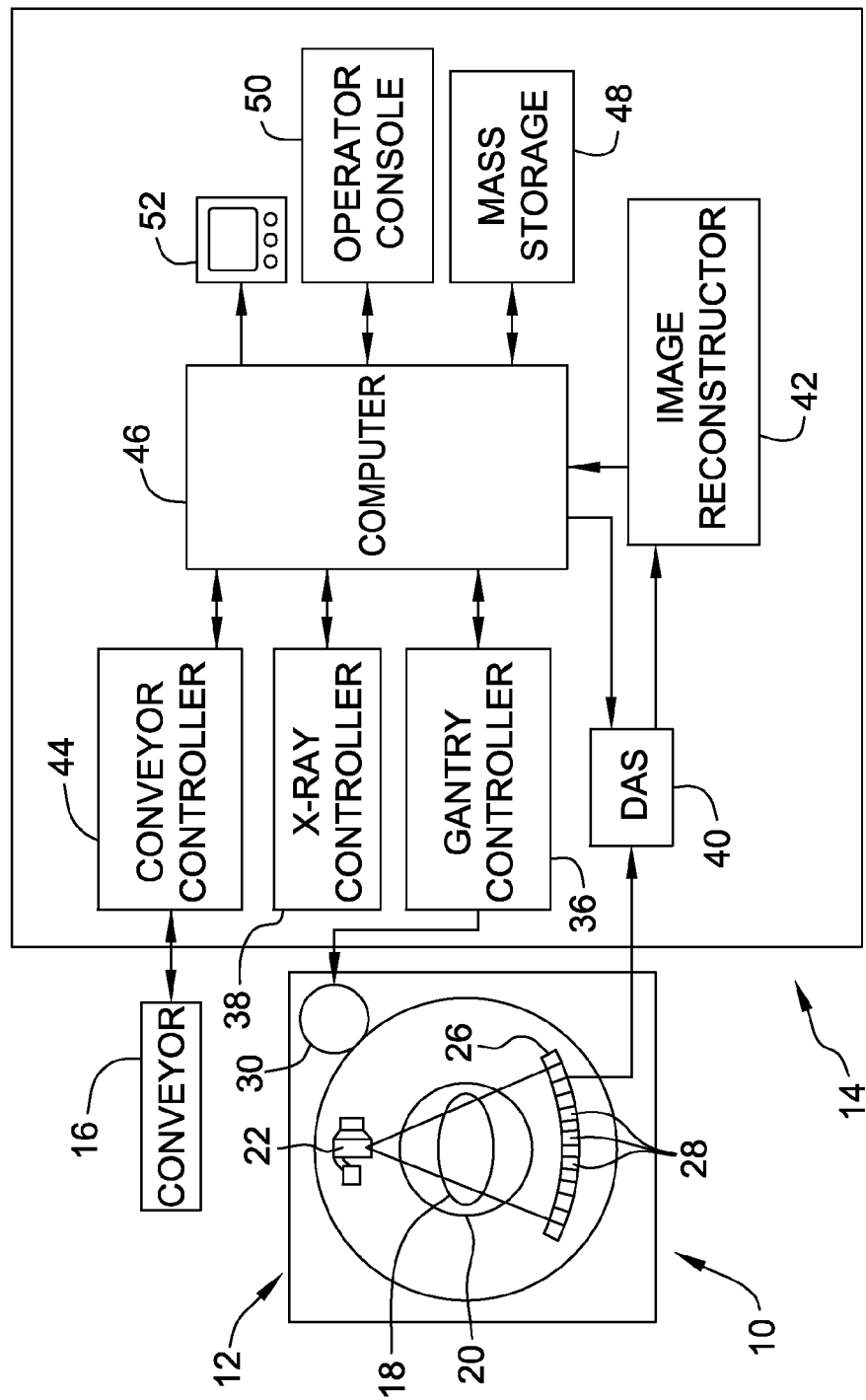
FIG. 2 is a schematic diagram of the CT imaging system shown in FIG. 1.

FIG. 1 is a perspective view of a computed tomography (CT) imaging system 10. FIG. 2 is a schematic diagram of CT imaging system 10 shown in FIG. 1. As shown in FIGS. 1 and 2, CT imaging system 10 includes a gantry system 12, which is representative of a CT scanner, a control system 14 (FIG. 2), and a motorized conveyor belt 16 for positioning an object 18, such as a piece of luggage, in a gantry opening 20 defined through gantry system 12. CT imaging system 10 may be, for example, a dual energy CT system. Gantry system 12 includes a radiation source 22, such as an x-ray source, that projects a fan beam of radiation, such as x-rays, toward a detector array 26 on the opposite side of gantry system 12. In the exemplary embodiment, radiation source 22 is an x-ray source configured to emit a fan beam of x-rays. Detector array 26 is formed by detector elements 28 (FIG. 2). Detector elements 28 are radiation detectors that each produce a signal having a magnitude that represents and is dependent on the intensity of the attenuated x-ray beam after it has passed through object 18 being imaged. During a helical scan that acquires x-ray projection data, a drive mechanism 30 (FIG. 2) rotates gantry system 12 along with the radiation source 22 and detector array 26 within a plane and around object 18 about an axis of rotation, while object 18 is moved through gantry system 12 in a z-direction 32 perpendicular to the plane of rotation.

Gantry system 12 and radiation source 22 are controlled by control system 14, which includes a gantry controller 36, an x-ray controller 38, a data acquisition system (DAS) 40, an image reconstructor 42, a conveyor controller 44, and a computer 46. Gantry controller 36 is operably coupled to drive mechanism 30, and controls the rotational speed and position of gantry system 12, while x-ray controller 38 provides power and timing signals to radiation source 22, and data acquisition system 40 acquires analog data from detector elements 28 and converts the data to digital form for subsequent processing. Image reconstructor 42 receives the digitized x-ray data from data acquisition system 40 and performs an image reconstruction process.

Computer 46 is in communication with the gantry controller 36, x-ray controller 38, and conveyor controller 44 whereby control signals are sent from computer 46 to controllers 36, 38, 44 and information is received from controllers 36, 38, 44 by computer 46. Computer 46 also provides commands and operational parameters to data acquisition system 40 and receives reconstructed image data from image reconstructor 42. In the exemplary embodiment, gantry system also includes a mass storage system 48, in which reconstructed image data may be stored for subsequent retrieval, an operator console 50, and a display device 52.

Communication between the various system elements of FIG. 2 is depicted by arrowhead lines, which illustrate a means for either signal communication or mechanical operation, depending on the system element involved. Communication amongst and between the various system elements may be obtained through a hardwired or a wireless arrangement. Computer 46 may be a standalone computer or a network computer and may include instructions in a variety of computer languages for use on a variety of computer platforms and under a variety of operating systems. Other examples of computer 46 include a system having a microprocessor, microcontroller or other equivalent processing device capable of executing commands of computer readable data or program for executing a control algorithm. Computer 46 may include, for example and without limitation, a processor(s), memory, storage, register(s), timing, interrupt(s), communication interfaces, and input/output signal interfaces, as well as combinations including at least one of the foregoing.

Figure 3:
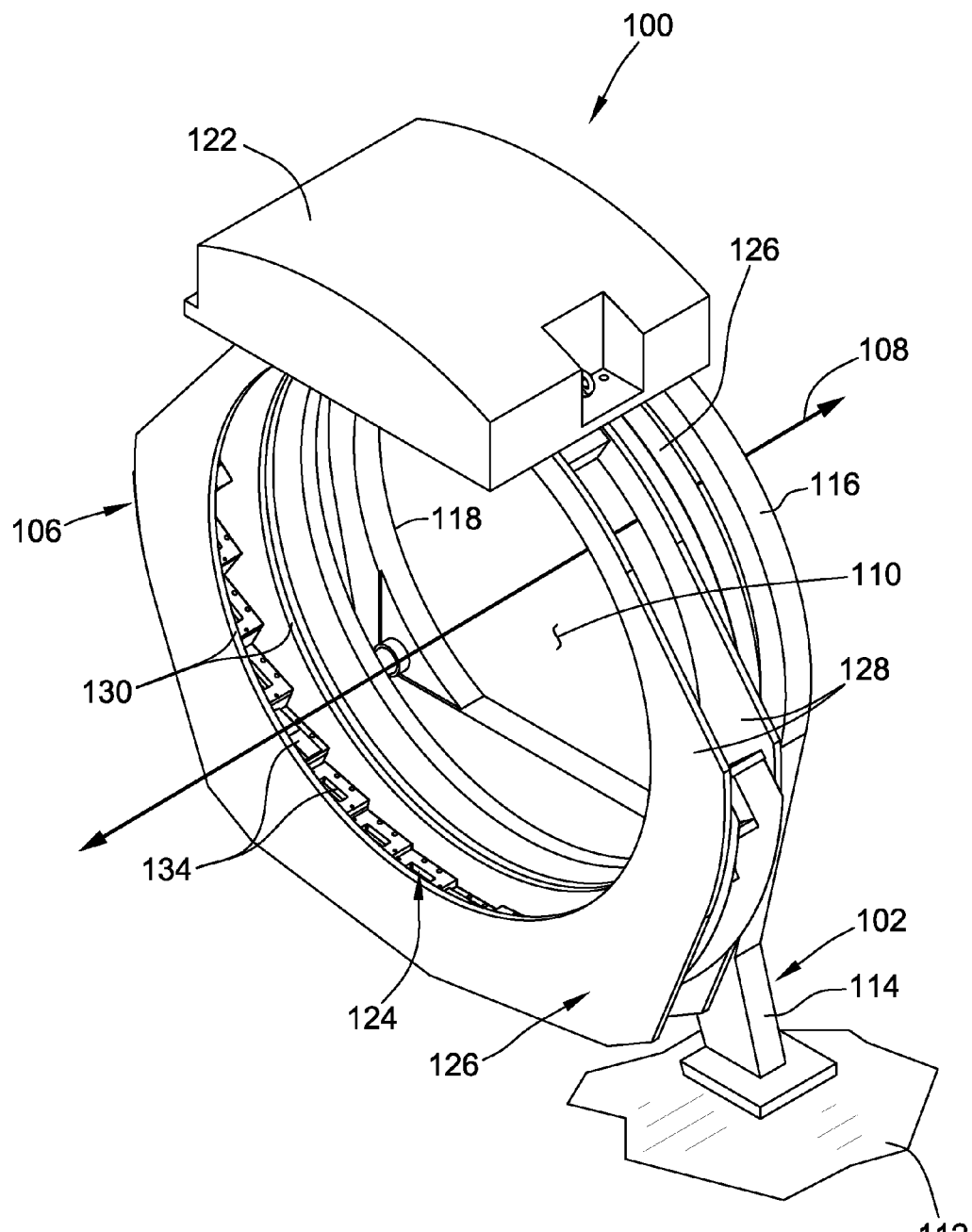
FIG. 3 is a front perspective view of an exemplary gantry system suitable for use in the CT imaging system of FIG. 1, the gantry system including a base and a gantry assembly.
Figure 4:
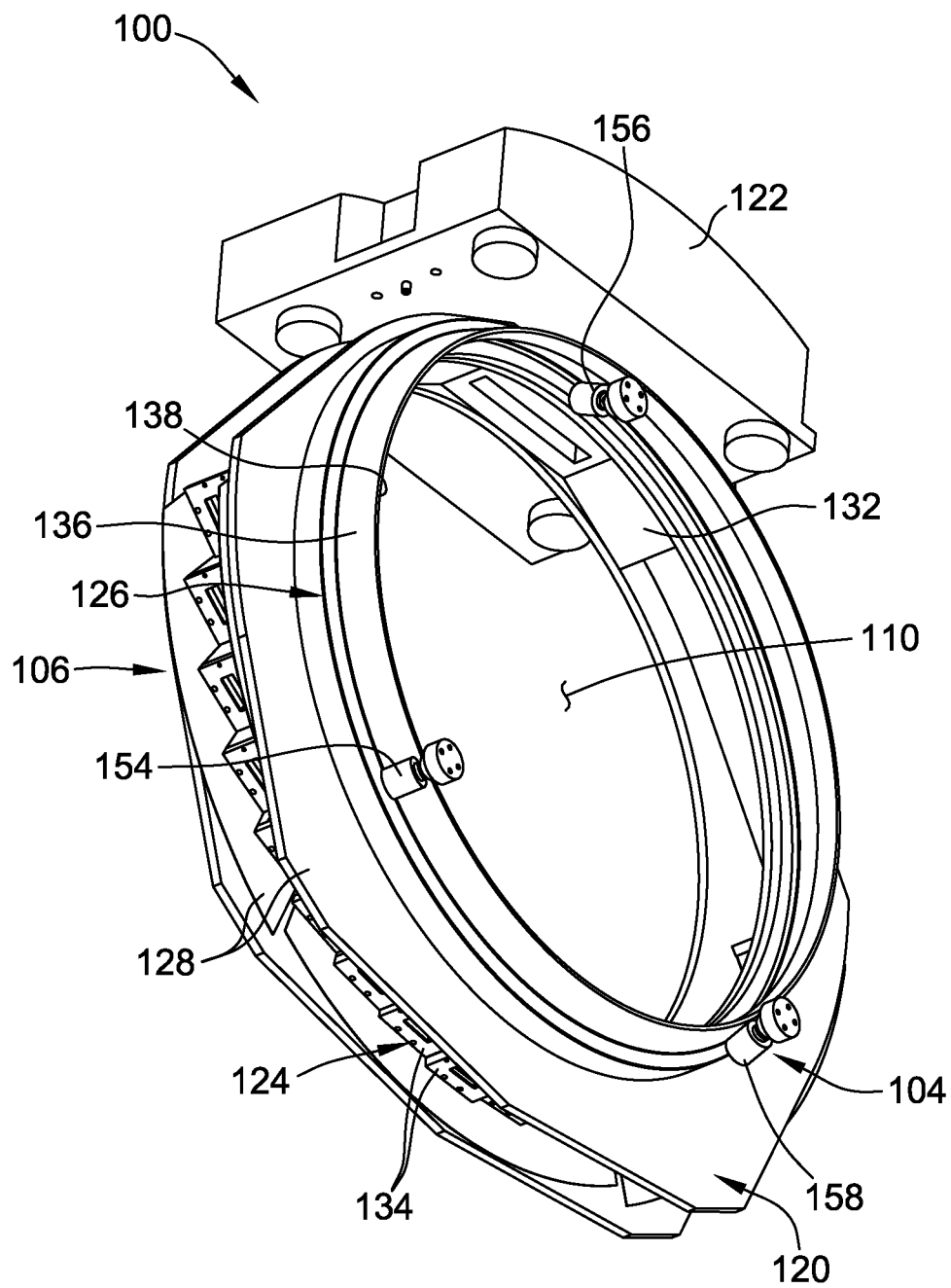
FIG. 4 is a rear perspective view of the gantry system of FIG. 3 with the base omitted to illustrate other components of the gantry system.
Figure 5:
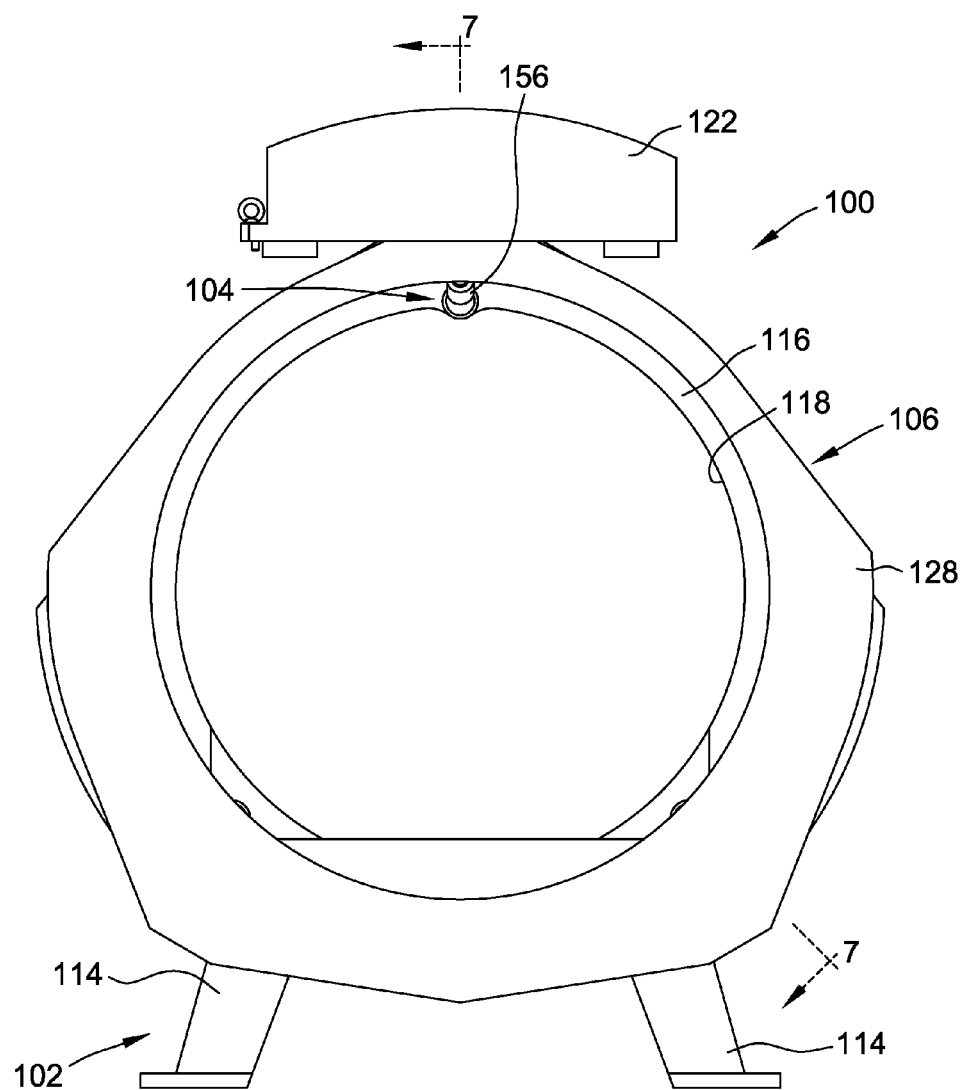
FIG. 5 is a front view of the gantry system of FIG. 3.
Figure 6:
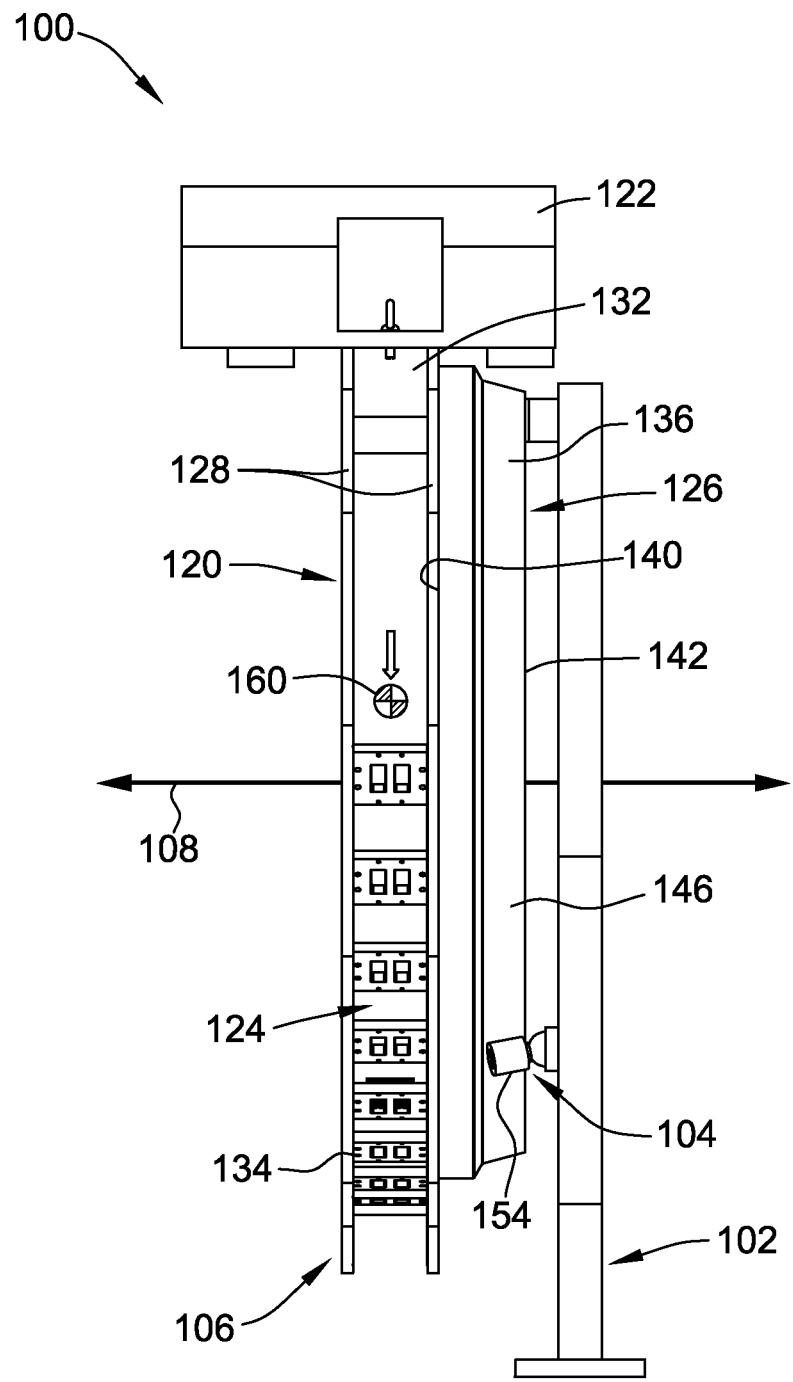
FIG. 6 is a side view of the gantry system of FIG. 3.
Figure 7:
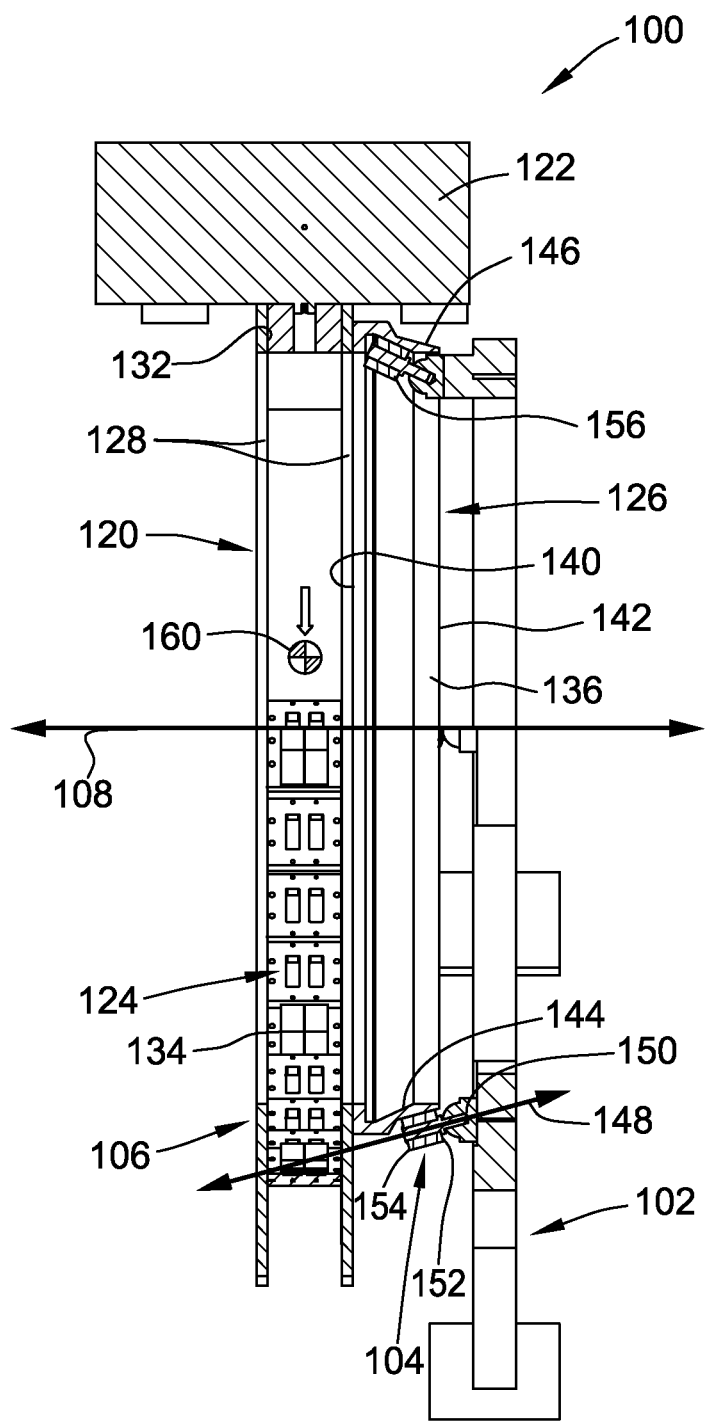
FIG. 7 is a cross-section of the gantry system of FIG. 3 taken along line 7-7 in FIG. 5.

FIG. 3 is a front perspective view of an exemplary gantry system 100 suitable for use with CT imaging system 10 of FIGS. 1 and 2. FIG. 4 is a rear perspective view of gantry system 100, FIG. 5 is front view of gantry system 100, FIG. 6 is a side view of gantry system 100, and FIG. 7 is a cross-section of gantry system 100 taken along line 7-7 in FIG. 5. In the exemplary embodiment, gantry system 100 includes a base 102, a plurality of rollers 104 coupled to base 102, and a gantry assembly 106 rotatably coupled to base 102 by rollers 104. Base 102 is not shown in FIG. 4 to illustrate other components of gantry system 100. Gantry assembly 106 is rotatably supported by rollers 104, and is configured to rotate about a gantry rotational axis 108 to collect imaging data from an object (not shown in FIG. 3) positioned within a central annular gantry opening 110 defined by gantry assembly 106. Gantry system 100 may also include a drive mechanism (not shown in FIG. 3), such as drive mechanism 30 (FIG. 2), operably coupled to gantry assembly 106 and configured to rotate gantry assembly 106 about gantry rotational axis 108. The drive mechanism may include any suitable equipment for transmitting rotational motion to gantry assembly 106 including, for example and without limitation, gears, drive wheels, drive belts, and combinations thereof.

Base 102 provides a fixed support for gantry assembly 106, and is fixed to a stationary structure, such as the surface or floor 112 of a facility in which gantry system 100 is used (e.g., an airport). In the exemplary embodiment, base 102 includes two legs 114 and an annular section 116 defining an opening 118 sized to permit the passage of objects, such as luggage, therethrough. Each leg 114 is fixed to a stationary structure using suitable fasteners, such as bolts, screws, or pins (not shown).

Gantry assembly 106 generally includes imaging equipment utilized to capture imaging data of objects positioned within gantry opening 110. In the exemplary embodiment, gantry assembly 106 includes a frame 120, a radiation source 122 coupled to frame, a detector array 124 coupled to frame 120, and an annular support rail 126 coupled to frame 120.

In the exemplary embodiment, frame 120 includes two substantially planer plates 128 spaced apart from one another in an axial direction of gantry system 100 (i.e., a direction parallel to gantry rotational axis 108). Each plate defines an annular opening 130 sized to permit the passage of objects, such as luggage, therethrough. In the exemplary embodiment, each plate 128 has substantially the same size and shape, although in other embodiments plates 128 may be sized and shaped differently from one another. Frame 120 may be constructed from any suitable material(s) that enables gantry system 100 to function as described herein including, for example and without limitation, steel, lead, and combinations thereof. In one embodiment, each plate 128 is constructed from steel and is lined with lead.

Radiation source 122 is coupled to frame 120 via a mount 132 positioned between plates 128. Mount 132 is coupled to plates 128 using suitable fasteners, such as bolts, screws, pins, and combinations thereof. Radiation source 122 is configured to emit radiation, such as x-rays, towards detector array 124, which is generally positioned at a diametrically opposite side of frame 120 from radiation source 122. In the exemplary embodiment, radiation source 122 is an x-ray source configured to project a fan beam of x-rays towards detector array 124.

Detector array 124 includes a plurality of detector elements 134 (also referred to herein as detectors) arranged in an arcuate pattern on a diametrically opposite side of frame 120 from radiation source 122. Each detector element 134 is coupled to frame 120 using suitable fasteners, such as bolts, screws, pins, and combinations thereof, and is positioned between plates 128. Each detector element 134 is configured to detect radiation emitted by radiation source 122. In particular, each detector element 134 is configured to produce a signal having a magnitude that represents and is dependent on the intensity of radiation from radiation source 122 incident on detector element 134.

Support rail 126 is coupled to frame 120, and is rotatably coupled to base 102 by rollers 104. Support rail 126 includes an annular sidewall 136 defining a central annular opening 138 sized to permit the passage of objects, such as luggage, therethrough. Support rail 126 is rotatably supported by rollers 104. The engagement between support rail 126 and rollers 104 enables support rail 126 and, more generally, gantry assembly 106 to rotate about gantry rotational axis 108 such that gantry system 100 can perform a helical scan on an object that passes through gantry opening 110.

As shown in FIGS. 6-7, support rail 126 includes a first end 140 coupled to one of plates 128 of frame 120 and a second end 142 distal from first end 140. Sidewall 136 extends axially between first end 140 and second end 142. Support rail 126 is shaped as a beveled ring, and sidewall 136 is canted with respect to gantry rotational axis 108. That is, sidewall 136 is a canted sidewall. As shown in FIGS. 6-7, sidewall 136 extends radially inward (i.e., towards gantry rotational axis 108) from first end 140 towards second end 142. Further, sidewall 136 includes a radial inner surface 144 and a radial outer surface 146, both of which are canted relative to gantry rotational axis 108. That is, radial inner surface 144 and radial outer surface 146 are each obliquely angled with respect to gantry rotational axis 108. Radial inner surface 144 and radial outer surface 146 may be canted at any suitable angle that enables gantry system to function as described herein. Suitable angles at which radial inner surface 144 and radial outer surface 146 may be canted include between about 5° and about 60°, more suitably between about 10° and about 45°, and, even more suitably, between about 10° and about 30°. Moreover, radial inner surface 144 and radial outer surface 146 may be canted at the same angle relative to gantry rotational axis 108, or radial inner surface 144 and radial outer surface may be canted at different angles. In the exemplary embodiment, radial inner surface 144 is canted at an angle of about 25° relative to gantry rotational axis 108, and radial outer surface 146 is canted at an angle of about 15° relative to gantry rotational axis 108.

Radial inner surface 144 and radial outer surface 146 are bearing surfaces configured to engage one or more rollers 104 to support the weight of gantry assembly 106, and enable gantry assembly 106 to rotate about gantry rotational axis 108. Support rail 126 and, in particular, sidewall 136, radial inner surface 144, and radial outer surface 146 may be constructed from one or more materials that facilitate limiting or minimizing friction along the interface between rollers 104 and radial inner surface 144 and radial outer surface 146. Suitable materials from which support rail 126 may be constructed include, but are not limited to, steel.

Rollers 104 are coupled to base 102, and are circumferentially spaced about gantry opening 110 and gantry rotational axis 108. Each roller 104 is configured to rotate about a roller rotational axis 148 (FIG. 7) to enable support rail 126 and frame 120 to rotate about gantry rotational axis 108. In the exemplary embodiment, each roller 104 includes a spindle 150 and an annular sleeve 152 having a central opening sized to receive spindle 150 therein. Sleeve 152 is configured to rotate about spindle 150 to enable support rail 126 and gantry assembly 106 to rotate about gantry rotational axis 108. Sleeve 152 and spindle 150 are suitably constructed from materials providing a low coefficient of friction between sleeve 152 and spindle 150 to reduce frictional losses between sleeve 152 and spindle 150.

The exemplary embodiment includes three rollers 104, including a first roller 154, a second roller 156, and a third roller 158. First roller 154 and third roller 158 each engage support rail 126 along radial outer surface 146, and second roller 156 engages support rail 126 along radial inner surface 144. In other embodiments, gantry system 100 may include any suitable number of rollers that enables gantry system 100 to function as described herein. As described in more detail herein, the arrangement and configuration of rollers 104 facilitate minimizing the number of rollers needed to rotatably support gantry assembly 106. In some embodiments, for example, gantry system may include less than six rollers 104, more suitably less than five rollers 104, and, even more suitably, less than four rollers 104. In some embodiments, such as the exemplary embodiment illustrated in FIGS. 3-7, gantry system 100 includes no more than three rollers 104.

Each roller 104 is oriented at an oblique angle with respect to gantry rotational axis 108. In particular, rotational axis 148 of each roller 104 is obliquely angled with respect to the gantry rotational axis 108. Suitable angles at which roller rotational axis 148 of each roller 104 may be oriented relative to gantry rotational axis 108 include between about between about 5° and about 60°, more suitably between about 10° and about 45°, and, even more suitably, between about 10° and about 30°. Moreover, each roller 104 may be oriented at the same angle relative to gantry rotational axis 108, or rollers 104 may oriented at different angles from one another. In the exemplary embodiment, each roller 104 is oriented at an angle that corresponds to the angle at which one of radial inner surface 144 and radial outer surface 146 are canted such that sleeve 152 of each roller 104 is substantially flush with a surface of sidewall 136. That is, each roller 104 that engages radial outer surface 146 of sidewall 136 is oriented at the same angle with respect to gantry rotational axis 108 as radial outer surface 146. Likewise, each roller 104 that engages radial inner surface 144 of sidewall 136 is oriented at the same angle with respect to gantry rotational axis 108 as radial inner surface 144. In the exemplary embodiment, first roller 154 and third roller 158 are each oriented at an angle of about 15° with respect to gantry rotational axis 108, and second roller 156 is oriented at an angle of about 25° with respect to gantry rotational axis 108.

Gantry assembly 106 has a mass and a center of gravity, indicated at 160 in FIGS. 6 and 7. First roller 154 and third roller 158 engage support rail 126 along radial outer surface 146 at points below center of gravity 160, and are configured to support the mass of gantry assembly 106. Thus, in the exemplary embodiment, first roller 154 and third roller 158 are load-bearing rollers.

As shown in FIGS. 6 and 7, center of gravity 160 is offset in an axial direction of gantry system 100 from the plane in which first roller 154 and third roller 158 engage support rail 126. Gantry assembly 106 is thus supported by rollers 104 in a cantilever-type arrangement, and the engagement of support rail 126 with first roller 154 and third roller 158 results in a rotational or cantilever moment on gantry assembly 106 in a direction generally away from base 102. In the orientation shown in FIGS. 6 and 7, the cantilever moment is in a counter-clockwise direction.

Second roller 156 is configured to counteract the cantilever moment on gantry assembly 106 resulting from the engagement of first and third rollers 154, 158 with support rail 126. In particular, second roller 156 is positioned in opening 138 (FIG. 4) defined by support rail 126, and engages support rail 126 along radial inner surface 144 at a point above center of gravity 160. The second roller 156 thereby counteracts the cantilever moment on gantry assembly 106 resulting from the engagement of first and third rollers 154, 158 with support rail 126, and maintains gantry assembly 106 in a generally upright orientation. That is, second roller 156 inhibits rotation of gantry assembly 106 about first roller 154 and third roller 158.

The cantilever moment on gantry assembly 106 urges radial inner surface 144 of sidewall 136 into contact with second roller 156, and facilitates maintaining continuous, flush contact between radial inner surface 144 of sidewall 136 and second roller 156. The configuration and arrangement of gantry assembly 106 and rollers 104 thereby facilities smooth rotation of gantry assembly 106 during use.

Further, by utilizing second roller 156 to counteract the cantilever moment of gantry assembly 106, gantry system 100 facilities minimizing the number of components needed to rotatably support gantry assembly. For example, the illustrated embodiment utilizes only three rollers 104 to rotatably support gantry assembly 106. Additionally, rollers 104 are easily accessible because they are not enclosed within a bearing enclosure (e.g., between two bearing rings). Rollers 104 can thus be more easily inspected, repaired, and/or replaced as compared to bearing components used in at least some known CT imaging systems. Moreover, rollers 104 of gantry system 100 may include general purpose rollers that are not custom made for a particular CT imaging system. Gantry system 100 thereby facilitates reducing the time and cost associated with maintaining the gantry systems of CT imaging systems.

Figure 8:
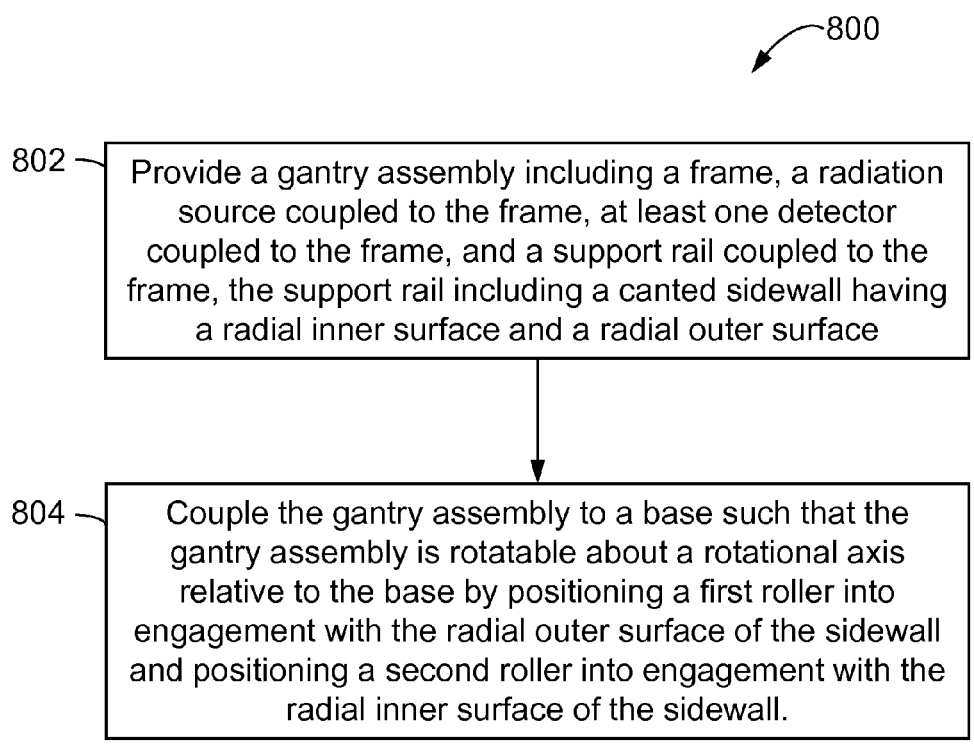
FIG. 8 is a flow chart of an exemplary method of assembling a gantry system.

FIG. 8 is a flow chart of an exemplary method of assembling a gantry system, such as gantry system 100 (FIGS. 3-7). The gantry system includes a base, such as base 102 (FIG. 3) and a plurality of rollers coupled to the base, such as rollers 104 (FIG. 4). The plurality of rollers includes a first roller and a second roller. The method includes providing 802 a gantry assembly, such as gantry assembly 106 (FIGS. 3-7), including a frame, a radiation source coupled to the frame, at least one detector coupled to the frame, and a support rail coupled to the frame. The support rail includes a canted sidewall having a radial inner surface and a radial outer surface. Method 800 further includes coupling 804 the gantry assembly to the base such that the gantry assembly is rotatable about a rotational axis relative to the base. Coupling 804 the gantry assembly to the base includes positioning the first roller into engagement with the radial outer surface of the sidewall and positioning the second roller into engagement with the radial inner surface of the sidewall. In some embodiments, coupling 804 the gantry assembly to the base includes positioning the first and second rollers into engagement with the sidewall such that that second roller is configured to counteract a cantilever moment of the gantry assembly resulting from engagement of the first roller with the radial inner surface of the sidewall.

In some embodiments, method 800 may further include coupling the plurality of rollers to the base. Coupling the plurality of rollers to the base may include coupling the plurality of rollers to the base such that the rollers are spaced circumferentially from one another about the rotational axis of the gantry assembly. In some embodiments, coupling the plurality of rollers to the base includes coupling the plurality of rollers to the base such that a rotational axis of each roller is obliquely angled with respect to the rotational axis of the gantry assembly. In some embodiments, coupling the plurality of rollers to the base may include coupling no more than three rollers to the base.

The systems and methods described herein facilitate assembling and maintaining gantry systems used in CT imaging systems, and further facilitate reducing the part count and overall cost of gantry systems used in CT imaging systems. For example, the gantry systems described herein utilize a gantry assembly rotatably supported by a plurality of rollers in a cantilever configuration. The gantry assembly includes a support rail having a canted sidewall with a radial inner surface and a radial outer surface. At least one of the rollers engages the radial outer surface to support the weight of the gantry assembly, and at least one of the rollers engages the radial inner surface to counteract a cantilever moment on the gantry assembly resulting from the at least one roller engaging the radial outer surface of the sidewall. The gantry system thus advantageously utilizes the cantilever moment of the gantry assembly to minimize the number of components needed to rotatably support the gantry assembly. Moreover, the rollers of the gantry systems described herein are not enclosed within a bearing enclosure (e.g., between two bearing rings), and are thus readily accessible for inspection, repairs, and replacement. Moreover, the rollers of the gantry systems described herein may include general purpose rollers that are not custom designed for a particular CT imaging system. The gantry systems described herein thereby facilitate reducing the time and cost associated with maintaining gantry systems of CT imaging systems.

Exemplary technical effects of the systems and methods described herein include at least one of: (a) reducing the overall part count and cost of rotatable gantry systems used in CT imaging systems; and (b) reducing the cost and time associated with repairing, replacing, and maintaining gantry systems used in CT imaging systems.

Exemplary embodiments of gantry systems for CT imaging systems and methods of assembling gantry systems are described above in detail. The methods and systems are not limited to the specific embodiments described herein, but rather, components of systems and/or steps of the methods may be utilized independently and separately from other components and/or steps described herein. Accordingly, the exemplary embodiment can be implemented and utilized in connection with many other applications not specifically described herein.

A computer, such as those described herein, includes at least one processor or processing unit and a system memory. The computer typically has at least some form of computer readable media. By way of example and not limitation, computer readable media include computer storage media and communication media. Computer storage media include volatile and nonvolatile, removable and nonremovable media implemented in any method or technology for storage of information such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Combinations of any of the above are also included within the scope of computer readable media.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A gantry system for use with a computed tomography imaging system, said gantry system comprising:

a frame defining an annular opening and configured to rotate about a rotational axis to collect imaging data from an object positioned within the opening;

a support rail coupled to said frame and comprising a canted sidewall having a radial inner surface and a radial outer surface; and a plurality of rollers rotatably supporting said support rail to enable rotation of said frame about the rotational axis, said plurality of rollers including a first roller engaging said radial outer surface and a second roller engaging said radial inner surface.

2. A gantry system in accordance with claim 1, wherein engagement of said first roller with said radial outer surface results in a cantilever moment on said frame, said second roller configured to counteract the cantilever moment on said frame.

3. A gantry system in accordance with claim 1, wherein each roller of said plurality of rollers is configured to rotate about a respective rotational axis, wherein the rotational axis of each of said rollers is obliquely angled with respect to the rotational axis of said frame.

4. A gantry system in accordance with claim 3, wherein the rotational axis of each of said rollers is angled at an angle of between about 5 degrees and about 60 degrees with respect to the rotational axis of said frame.

5. A gantry system in accordance with claim 1, wherein said plurality of rollers further includes a third roller engaging said radial outer surface of said sidewall, wherein each of said rollers is spaced circumferentially about the rotational axis of said frame from each other roller.

6. A gantry system in accordance with claim 1, wherein said plurality of rollers includes no more than three rollers.

7. A gantry system in accordance with claim 1, wherein said support rail includes a first end coupled to said frame and a second end, said sidewall extending axially between said first and second ends, wherein said sidewall extends radially inward from the first end towards the second end.

8. A gantry system in accordance with claim 1, wherein said frame comprises a pair of plates spaced apart from one another in an axial direction, said support rail coupled to one of said plates.

9. A gantry system in accordance with claim 1, further comprising:

a radiation source coupled to said frame, said radiation source configured to emit radiation; and at least one detector coupled to said frame, said at least one detector configured to detect radiation emitted by said radiation source.

10. A computed tomography (CT) imaging system comprising:

a base;

a plurality of rollers coupled to said base, said plurality of rollers including a first roller and a second roller; and a gantry assembly rotatably coupled to said base by said plurality of rollers, said gantry assembly comprising:

a frame;

a radiation source coupled to said frame;

at least one detector coupled to said frame and configured to detect radiation emitted by said radiation source; and a support rail coupled to said frame and including a canted sidewall having a radial inner surface and a radial outer surface, wherein said first roller engages said radial outer surface and said second roller engages said radial inner surface.

11. A CT imaging system in accordance with claim 10, wherein engagement of said first roller with said radial outer surface results in a cantilever moment on said gantry assembly, said second roller configured to counteract the cantilever moment on said gantry assembly.

12. A CT imaging system in accordance with claim 10, wherein each roller of said plurality of rollers is configured to rotate about a respective rotational axis, wherein the rotational axis of each of said rollers is obliquely angled with respect to the rotational axis of said frame.

13. A CT imaging system in accordance with claim 10, further comprising a drive mechanism operably coupled to said gantry assembly and configured to rotate said gantry assembly about the rotational axis.

14. A CT imaging system in accordance with claim 10, wherein said plurality of rollers includes no more than three rollers.

15. A CT imaging system in accordance with claim 10, wherein said support rail includes a first end coupled to said frame and a second end, said sidewall extending axially between said first and second ends, wherein said sidewall extends radially inward from the first end towards the second end.

16. A method of assembling a gantry system including a base and a plurality of rollers coupled to the base, the plurality of rollers including a first roller and a second roller, said method comprising:

providing a gantry assembly including a frame, a radiation source coupled to the frame, at least one detector coupled to the frame, and a support rail coupled to the frame, the support rail including a canted sidewall having a radial inner surface and a radial outer surface; and coupling the gantry assembly to the base such that the gantry assembly is rotatable about a rotational axis relative to the base, wherein coupling the gantry assembly to the base includes positioning the first roller into engagement with the radial outer surface of the sidewall and positioning the second roller into engagement with the radial inner surface of the sidewall.

17. A method in accordance with claim 16, wherein coupling the gantry assembly to the base includes positioning the first and second rollers into engagement with the sidewall such that that second roller is configured to counteract a cantilever moment of the gantry assembly resulting from engagement of the first roller with the radial outer surface of the sidewall.

18. A method in accordance with claim 16, further comprising coupling the plurality of rollers to the base, wherein coupling the plurality of rollers to the base includes coupling no more than three rollers to the base.

19. A method in accordance with claim 16, wherein each roller of the plurality of rollers is configured to rotate about a respective rotational axis, the method further comprising coupling the plurality of rollers to the base such that the rotational axis of each roller is obliquely angled with respect to the rotational axis of the gantry assembly.

20. A method in accordance with claim 16, further comprising coupling the plurality of rollers to the base such that each of the rollers is spaced circumferentially about the rotational axis of the gantry assembly from each of the other rollers.

* * * * *